United States Patent [19]
Porzilli

[11] Patent Number: 5,336,209
[45] Date of Patent: * Aug. 9, 1994

[54] MULTI-FUNCTION WOUND PROTECTION BANDAGE AND MEDICANT DELIVERY SYSTEM WITH SIMULTANEOUS VARIABLE OXYGENATION

[76] Inventor: Louis B. Porzilli, P.O. Box 374, Rockaway, N.J. 07866

[*] Notice: The portion of the term of this patent subsequent to Oct. 27, 2009 has been disclaimed.

[21] Appl. No.: 966,683

[22] Filed: Oct. 26, 1992

Related U.S. Application Data

[63] Continuation-in-part of Ser. No. 465,968, Apr. 6, 1990, Pat. No. 5,158,555.

[51] Int. Cl.$^5$ ............................................. A61F 13/02
[52] U.S. Cl. ..................................... 604/307; 602/47; 602/59; 128/888
[58] Field of Search ....................... 604/304, 307, 308; 128/888; 602/43, 47, 58, 59; 606/213, 214, 215

[56] References Cited

U.S. PATENT DOCUMENTS

| | | | |
|---|---|---|---|
| 1,920,808 | 8/1933 | Sander | 604/307 |
| 3,043,301 | 7/1962 | Plantinga et al. | 602/59 |
| 4,646,731 | 3/1987 | Brower | 606/215 |
| 4,875,473 | 10/1989 | Alvarez | 602/58 |
| 4,972,829 | 11/1990 | Knerr | 602/47 |
| 5,018,515 | 5/1991 | Gilman | 602/58 |
| 5,158,555 | 10/1992 | Porzilli | 604/307 |

Primary Examiner—Randall L. Green
Assistant Examiner—Paul Prebilic
Attorney, Agent, or Firm—Richard T. Laughlin

[57] ABSTRACT

A protective wound bandage which allows for the body's natural epitheliazation process to be enhanced by the function of said bandage in the following ways. A non-stick surface is provided to make contact with the wound. An absorbent pad is provided for body fluid drainage. The skin adhesive surfaces of the flexible plastic strip which can be made to any dimension, in combination with the pad act to protect and cohesively and coherently bind the wound edges together. The removably, reattachable, tear tab provides the ability to regulate and monitor oxygen flow to the injury site. The pad, in either the standard or perforated form acts to protect against shock and also acts as an medicant delivery system. The bandage acts as a medicant delivery system and is also simultaneously, variably, oxygenatable. The bandage is engineered to operate in either the dry or medicated versions.

20 Claims, 1 Drawing Sheet

MULTI-FUNCTION WOUND PROTECTION BANDAGE AND MEDICANT DELIVERY SYSTEM WITH SIMULTANEOUS VARIABLE OXYGENATION

This is a continuation-in-part of copending application(s) Ser. No. 07/465,968 filed on Apr. 6, 1990, now U.S. Pat. No. 5,158,555 issued Oct. 27, 1992.

BACKGROUND OF THE INVENTION

1. Field of the Invention

This invention relates to a multilayer dressing which allows for increased ventilation. The removal of the top dressing increases the rate of oxygenation, improving the rate of epidermal healing.

2. Description of the Prior Art

U.S. Pat. No. 209,560, issued to Griffith relates to an improved method of plaster type bandages. Another plaster type bandage is disclosed in Sander's U.S. Pat. No. 1,920,808. An improved surgical bandage is disclosed in U.S. Pat. No. 974,294 utilizing woven fabric and gelatin-glycerin compound. Shepherd, U.S. Pat. No. 3,428,043 discloses a hydrophilic hydrogel material reinforced with a coextensive sheet of fabric. U.S. Pat. No. 4,884,563 discloses an improved bandage which has a non-stretchable, yet flexible, plastic cover sheet. In U.S. Pat. No. 3,687,136, a bandage is disclosed which allows the user to match their skin color. U.S. Pat. No. 3,875,937 to Schmitt discloses a wound dressing treated with a polyhydroxyacetic ester which becomes embedded in a wound and is later replaced by living tissue.

In Alvarez, U.S. Pat. No. 4,875,473, a multi-layer wound dressing is providing which facilitates healing using hypoxia followed by an aerobic environment. The Alvarez patent does not allow for monitoring of the wound nor is it provide for moisture to be drawing away from the wound.

The Thompson patent, U.S. Pat. No. 4,649,909, the emphasis is drawing moisture away from the wound. The primary dressing component 13 is secured to the skin of a patient. The absorbent material 12 is removably placed over the primary dressing and can be changed, as needed, without removal of the primary dressing component 13. The layers of the bandage are held in place by the fibrous backing 10. The although removable for changing, the Thompson patent does not allow for oxygenation.

Although the dressings shown in these references offer some advantages, they have not been totally successful in providing the needed ventilation which increases the epidermal healing.

SUMMARY OF THE INVENTION

A protective dressing is disclosed which has a covering portion, of at least two sections, a removable tear tab cover, a gauze layer, positioned to be in contact with said covering portion; an absorbent pad adjacent the gauze layer, and a non stick layer. The absorbent pad has perforations which form wicking cells creating anaerobic and aerobic oxygen chambers and medication reservoirs. A section of the covering portion, removable perforated cover, absorbent pad and non-stick layer are perforated to allow for air flow. The perforations are of sufficient size to provide for ventilation and are aligned with one another. The covering portion has a skin releasable adhesive. The removable perforated cover has surface areas on its periphery which contain releasable, resealable adhesive. In one embodiment the removable perforated cover allows visibility of the wound. The removable perforated cover can be temporarily removed to monitored the wound and reaffixed to act as a vent to provide oxygen to the injury to enhance epithelization and regulate oxygenation. After a period of time, based on the progress of the anaerobic moist wound healing phase the removable perforated cover is removed to allow for increased oxygenation and aerobic healing. The absorbent pad further includes medication including one or more of elastin, epidermal growth factor(s), Aloe and Vitamin E in variable combinations and concentrations. The dressing can be manufactured from biodegradable materials if so desired.

In another more basic hence more easily manufactured embodiment, a standard absorbent pad is used without the perforations.

BRIEF DESCRIPTION OF THE DRAWINGS

The specification and disclosed invention will be better understood when read in reference to the drawing in which.

DETAILED DESCRIPTION OF THE EMBODIMENT

Figure 1:
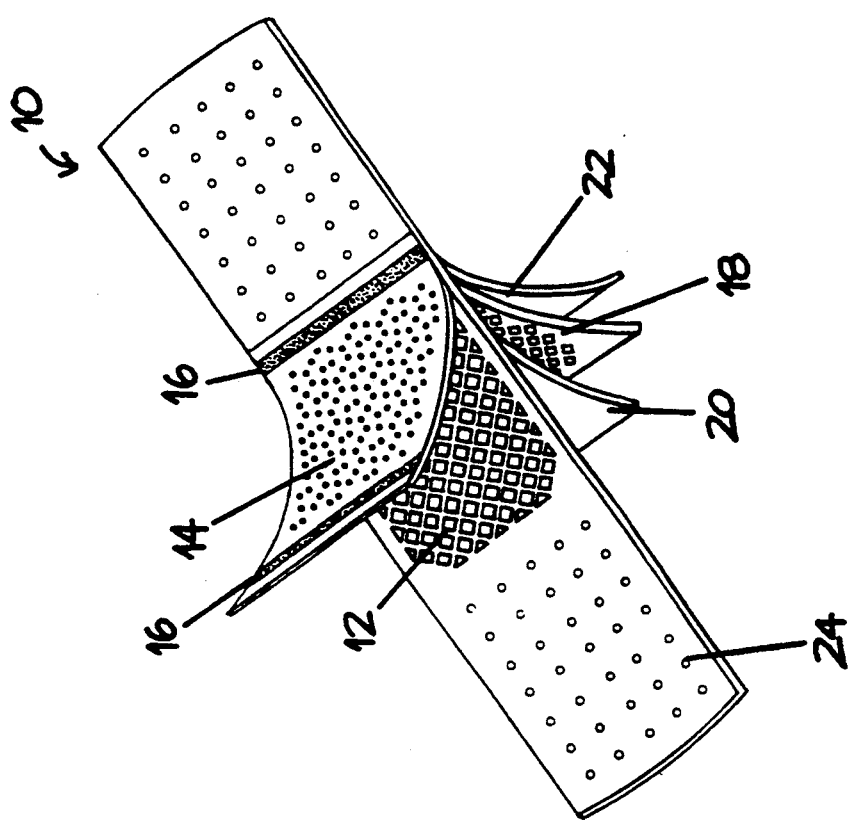
FIG. 1 is a perspective view of the device of the instant invention.

In FIG. 1 the assembled protective dressing or bandage 10 is illustrated with the separate sections pulled away from the main bandage 10 for ease of description. The covering portion or strip 24 illustrated is a single strip of non adhesive plastic or fabric which has been covered with a skin release adhesive, as known in the prior art. In the preferred embodiment, the skin release adhesive covering strip 24 would be manufactured in a biodegradable material. The ventilation perforations 12 are out into the non stick adhesive covering strip 24 at time of manufacture. The ventilation perforations 12 allow for added ventilation and oxygenation for the wound to assist in improved epitheliazation. The ventilation perforations 12 as shown in FIG. 1 are cut in diamonds. It should be noted, however, that this is only one configuration which the perforations can take and any pattern, size or number can be used to obtain specific results, providing they do not endanger the integrity of the bandage 10. The covering strip 24 also serves as an adhesive restraint clamp to maintain the edges of the wound adjacent one another and allows for stratified, cohesive and cohesion of all layers of the skin resulting from the flexible binding effect of the protective adhesive covering strip 24 and protects the site from further injury. In the instant disclosure, the medical terms for adhesive and clamp are used as follows: "adhesive . . . 1. sticky; tenacious. 2. a substances that cause close adherence of adjoining surfaces." and "clamp . . . 1. any device used to grip, join, compress, or fasten parts." *Dorland's Illustrated Medical Dictionary*, W. B. Saunders Co., Philadelphia, 1988. By maintaining the wound edges proximate to one another, in combination with the increased healing due to the anaerobic atmosphere then ventilation, further decreases the healing time as well as reduces the chances of scarring when used with the medications as previously described.

The tear tab cover 14 is removably placed over the ventilation perforations 12 to provide wound closure with minimal ventilation. The tear tab cover 14 is, in a preferred embodiment, manufactured from a translucent, opaque or clear biodegradable material. Other materials can be substituted providing they provide the same minimal air permeability benefits and meet the same medical standards which are required. The tear tab cover 14 is provided with adhesive strips 16 which affix the tear tab cover 14 to the covering strip 24. The adhesive strips 16, as illustrated herein, are placed at opposite ends of the perforated cover 14, however they strips 16 can be placed along the entire periphery of the tear tab cover 14. The percentage of the periphery which requires adhesive strips is largely dependent upon the configuration and size of the tear tab cover and pad configuration. A larger or multi-sided cover would require a greater percentage of its periphery covered by adhesive strips than would a small, square configuration. The adhesive strips 16 should be a material which retains its adhesive qualities to allow the tear tab cover 14 to be removed and then readhered to the plastic strip 24. As an alternative, the perforated cover can be manufactured from the same material as the covering strip 24 and the tear tab cover 14 removed for viewing the wound. The tear tab cover 14 can be perforated to allow for additional oxygen transmission during the aerobic stage. Additional tear tab covers 14 can be provided by the manufacturer to allow for replacement of the original cover 14. In an alternate embodiment the tab cover is a sliding member which moves on a track within the bandage. This alternate provides for a greater range of control in the oxygenation by allowing the sliding member to open the desired amount.

The removability of the tear tab cover 14 allows for additional oxygenation allowing for enhanced epitheliazation. The perforations can range in size from micro perforations to approximately those of a standard bandage. The perforations in the perforated cover 14 must serve to control air permeability and therefore must remain in the size range of a standard bandage or below. A recent study of burn victims that there was an improved rate of epidermal healing when treated in a hyperbaric chamber. The instant invention takes advantage of the increased rate of epidermal healing through added oxygenation by allowing increased ventilation upon removal of the tear tab cover 14.

The gauze layer 20 is placed adjacent the non stick adhesive plastic strip 24 to provide protection against macro foreign particles once the tear tab cover 14 is removed. The gauze layer 20 is manufactured from multiple layers of gauze or synthetic mesh as well known in the prior art. The gauze layer 20 is placed directly adjacent the ventilation perforations 12. The gauze layers 20 also acts to limit transmigration of bacteria and other foreign particles. The gauze 20 can also be manufactured of a transparent synthetic material. The term gauze is used herein to indicate "1. a very thin, light, loosely woven material, usually of silk or cotton: also applied to other material of similar open texture; as wire gauze." *Webster's New Twentieth Century Dictionary*, Second Edition. New World Dictionaries/Simon and Schuster, New York, N.Y., 1983.

The absorbent perforated pad 18 is placed adjacent the gauze layer. The absorbent perforated pad 18 is manufactured from a absorbent material which has been machine perforated. The perforations in the absorbent pad 18 are larger than those in the tear tab cover 14 to allow for maximum air permeability. During the perforating process, channels are automatically created. The channels create a wicking action which draws the moisture and fluids from the wound. The channels additionally create cells and pathways for retaining medication, especially when applied in a cream, liquid or gel form. The channels also serve to create as aerobic oxygenation cells, allowing for individual chambers where the air can come in contact the wound. Medication can be added to the absorbent perforated pad 18 and is dependent upon the method of manufacture. In a liquid form the medication can contain, as examples, any one of or a combination of elastin, Epidermal Growth Factor(s), Aloe and/or Vitamin E, or any other medication which meets the medical requirements or standard of the day. The concentrations and combinations can vary depending upon the type of wound. A heat sensitive melting gel can be applied to the pad filling the cells for release on contact with the skin. The foregoing examples are provided as examples only and any versed in the prior art will be knowledgeable in additional medications to be used in combination with the instant disclosure. The absorbent perforated pad 18 is shown with diamond cuts, however, as previously noted above, the configuration illustrated is for convenience only and other shaped cuts can be used.

As an alternative, a standard bandage pad can be used to replace place the separate perforated pad 18 and the gauze layer 20. The use of a standard pad substantially cuts the cost of the bandage 10, however a standard pad would not provide the same level of air permeability of the preferred pad and would drastically reduce the oxygenative qualities and increase the anaerobic affect.

A non-stick transparent material 22 is placed over the absorbent perforated pad 18 to prevent the absorbent perforated pad 18 from sticking to the wound. The non-stick transparent material 22 can be placed over the absorbent perforated pad 18 and secured to the non-stick plastic strip 24 at the time of manufacturer. As an alternative, the non-stick transparent material 22 can be wrapped, or shrink wrapped, around the absorbent perforated pad 18 and gauze layer 20 and secured to the non-stick plastic strip 24 as a unit. Another alternative would be to secure the non-stick transparent material 22 directly to the absorbent perforated pad 18, covering the pad either fully or partially. The non-stick transparent material 22 must be air permeable and would generally be a perforated clear material known in the prior art.

It is critical, to gain optimal air permeability, that the gauze layer 20, absorbent perforated pad 18 and the non-stick transparent material 22 be placed directly adjacent to and lined up with the ventilation perforations 12, in the non-stick adhesive plastic strip 24. The perforated cover 14 adjacent to and lined up with the macro ventilation perforations 12 on the opposite side of the adhesive plastic strip 24. The nonalignment of the layers inhibits the second stage oxygenation of the wound and the increased epitheliazation.

In instant disclosure, the term covering strip is used, however it should be noted that the bandage can be of any configuration, as it is the accumulative elements and controlling air permeability which provides the advantages.

What is claimed is:

1. A protective dressing having a covering portion, said covering portion having a first side and a second side, and being divided into at least two sections, wherein A. the second section of at least two sections of said covering portion has a removable cover affixed to said first side;

B. said second section of the second side of said covering portion having a gauze layer, said gauze layer positioned to be in contact with said covering portion, said gauze layer limiting transmigration of bacteria and other macrophages;

C. an absorbent pad adjacent to said gauze layer, said absorbent pad having perforations, thereby forming fluid wicking channels between said perforations, said wicking channels creating anaerobic and aerobic oxygen chambers and medication reservoirs;

D. a non-stick layer adjacent to said absorbent pad, said non-stick layer covering at least a portion of said gauze layer;

wherein said second section of said covering portion, said absorbent pad and said non-stick layer are perforated to allow for air flow, said perforations being of sufficient size to provide for ventilation, said perforations being aligned with one another.

2. The protective dressing of claim 1 wherein the first section of said at least two sections has skin releasable adhesive on said second side.

3. The protective dressing of claim 1 wherein said removable cover has surface areas on its periphery, said surface areas containing releasable, resealable adhesive.

4. The protective dressing of claim 1 wherein said removable cover allows visibility of the wound.

5. The protective dressing of claim 1 wherein said removable cover is translucent.

6. The protective dressing of claim 1 wherein said removable cover is biodegradable.

7. The protective dressing of claim 3 wherein said removable cover is configured to be removed and reaffixed whereby said wound can be monitored.

8. The protective dressing of claim 1 wherein said removable cover can be removed and reaffixed to act as a vent to provide oxygen to the injury to enhance epitheliazation and regulate oxygenation.

9. The protective dressing of claim 1 wherein said absorbent pad further includes medication comprising one or more of elastin, epidermal growth factors, Aloe and Vitamin E in variable concentrations.

10. The protective dressing of claim 1 wherein said removable cover is perforated.

11. The method of increasing the rate of epitheliazation of a wound through anaerobic to increased oxygenation comprising, providing a protective dressing, said protective dressing consisting of:

a covering portion, said covering portion having a first side and a second side, each side having at least two sections, wherein the second section of said at least two sections in perforated;

said second section of said first side of said covering portion having a removable, reaffixable, perforated cover, said removable, perforated cover having adhesive areas on at least a portion of its periphery;

said second section of said second side of said covering portion having a gauze layer to provide atmospheric oxygenation, said gauze layer being positioned to be in contact with said covering portion;

an absorbent pad adjacent to said gauze layer, said absorbent pad being perforated to allow for air flow, thereby forming wicking channels between said perforations, said wicking channels absorbing moisture and body fluids from the wound, a non-stick layer adjacent to said absorbent pad, said non-stick layer being perforated to allow for air flow, said non-stick layer covering at least a portion of said absorbent pad;

skin release adhesive, said skin release adhesive being on said first section of said second side of said covering portion;

said second portion of said covering portion, said absorbent pad and said non-stick layer being perforated to allow for air flow, said perforations being of sufficient size to provide for ventilation, and said perforations being aligned with one another;

applying said protective dressing to said wound as an adhesive restraint clamp thereby promoting stratified layered coherent cellular cohesion by securing the walls of the wound together;

maintaining said removable cover affixed to said protective dressing to decrease oxygenation;

removing said removably affixed cover to act as a vent to allow for increased oxygenation to enhance epitheliazation; and reaffixing said removably affixed cover to decrease oxygenation thereby regulating and monitoring oxygenation.

12. The protective dressing of claim 1 wherein said removable cover is transparent.

13. The method of increasing epitheliazation of a wound of claim 11 wherein said removable cover is at least translucent whereby the wound can be viewed.

14. The method of increasing epitheliazation of a wound of claim 11 wherein said removable cover is opaque.

15. The method of increasing epitheliazation of a wound of claim 11 wherein said removable cover is temporarily removed for a time sufficient to monitor said wound.

16. The method of increasing epitheliazation of a wound of claim 11 wherein said removable cover is removed for a time sufficient to allow for increased oxygenation and aerobic healing.

17. The method of increasing epitheliazation of a wound of claim 16, wherein said removable cover is removed after a predetermined time period, thereby enhancing epitheliazation and regulating oxygenation.

18. The method of increasing epitheliazation of a wound of claim 11 wherein said perforations in said absorbent pad, said covering portion, gauze layer and said non-stick layer are sized to allow air flow through said absorbent pad, plastic strip, gauze layer and non-stick layer.

19. A protective dressing having a covering portion, said covering portion having a first side and a second side, and being divided into at least two sections, wherein A. the second section of at least two sections of said covering portion has a removable perforated cover affixed to said first side;

B. said second section of said second side of said covering portion having an absorbent pad positioned adjacent to the said covering portion;

C. a non-stick layer adjacent to said absorbent pad, said non-stick layer covering at least a portion of said gauze layer;

wherein said second portion of said covering portion and said removable perforated cover are perforated to allow for air flow, said perforations being of sufficient size to provide for ventilation, said perforations being aligned with one another.

20. The protective dressing of claim 1 wherein said removable cover is perforated.

* * * * *